United States Patent [19]

Chen et al.

[11] Patent Number: 5,004,691
[45] Date of Patent: Apr. 2, 1991

[54] METHOD FOR PRODUCING THE ACCI RESTRICTION ENDONUCLEASE AND METHYLASE

[75] Inventors: Shu-zi Chen, Cambridge; Geoffrey G. Wilson, Boxford, both of Mass.

[73] Assignee: New England Biolabs, Inc., Beverly, Mass.

[21] Appl. No.: 133,957

[22] Filed: Dec. 17, 1987

[51] Int. Cl.$^5$ ............... C12N 15/52; C12N 9/22; C12N 1/21

[52] U.S. Cl. .................. 435/172.3; 435/199; 435/252.33; 435/320.1; 536/27; 935/29; 935/73; 935/80

[58] Field of Search ............ 435/172.3, 199, 320, 435/252.3, 252.33; 935/29, 73, 80, 82; 536/27

[56] References Cited

PUBLICATIONS

Greene, P. J. et al., (1981), J. Biol. Chem., 256(5), 2143–2153.
Newman, A. K., et al., (1981), J. Biol. Chem. 256(5), 2131–2139.
Schoner, B., et al., (1983), Gene 24, 227–236.
Walder, R. Y., et al., (1984), J. Biol. Chem. 259(12), 8015–8026.
Roberts, R. J., (1984), Nucleic Acids Res. 12, r167, r168, r204.
Lunnen, K. D., et al., (1988), Gene 74, 25–32.
Wilson, G. G., (1988), Gene 74, 281–289.
Wilson, G. G., (1988), Trends in Genetics 4(11), 314–318.

*Primary Examiner*—Elizabeth C. Weimar
*Assistant Examiner*—Charles L. Patterson, Jr.
*Attorney, Agent, or Firm*—Gregory D. Williams; David G. Conlin

[57] ABSTRACT

The present invention is directd to a method for cloning and producing the AccI restriction endonuclease by (1) introducing the restriction endonuclease gene from into a host whereby the restriction gene is expressed; (2) fermenting the host which contains the plasmid encoding and expressing the AccI restriction endonuclease activity, and (3) purifying the AccI restriction endonuclease from the fermented host which contains the plasmid encoding and expressing the AccI restriction endonuclease activity.

9 Claims, 4 Drawing Sheets

FIG. I

METHOD FOR PRODUCING THE ACCI RESTRICTION ENDONUCLEASE AND METHYLASE

BACKGROUND OF THE INVENTION

The present invention relates to clones for the AccI restriction endonuclease and modification methylase, and to the production of these enzymes from the clones.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the by means of which genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria tend to possess at most only a small number restriction endonucleases per species. The endonucleases typically are named according to the bacteria from which they are derived. Thus, the species *Haemopilus aegyptius*, for example synthesizes 3 different restriction endonucleases, named HaeI, HaeII and HaeIII. These enzymes recognize and cleave the sequences (AT)GGCC(AT),PuGCGPy and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The break-up that takes place disables many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclese, but instead of breaking the DNA, they chemically modify one or other of the nucleotides within the sequence by the addition of a methyl group. Following this methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-4}$ to $10^{-3}$. Preferably, the method should be selective, such that the unwanted majority of clones are destroyed while the rare desirable clones survive.

Type II restriction-modification systems are being cloned with increasing frequency. The first cloned systems used bacteriophage infection as a means of identifying or selecting restriction endonuclease clones (EcoRII Kosykh et al., Molec. gen. Genet 178: 717–719, (1980); HhaII: Mann et al., Gene 3: 97–112, (1978); PstI: Walder et al.,*Proc. Nat. Acad. Sci. USA* 78 1503 1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucleic Acids Res. 12:3659–3676, 1984; PaeR7: Gingeras and Brooks, *Proc. Natl. Acad. Sci. USA* 80:402–406, 1983; Theriault and Roy, Gene 19:355–359 1982; PvuII: Blumenthal et al., *J.Bacteriol.* 164:501–509, 1985).

A third approach, and one that is being used to clone a growing number of systems, involves selecting for an active methylase gene referring to our Patent application No.: 707079 (BsuRI: Kiss et al., *Nucleic Acids Res.* 13:6403–6421, 1985). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., *Gene* 10:219–225 (1980); BcnI: Janulaitis et al, *Gene* 20: 197–204 Kiss and Baldauf, *Gene* 21: 111–119, (1982); BsuRI: Kiss and Bal Auf, *Gene* 21: 111–14, 119, (1983); and MspI: Walder et al., J. Biol. Chem. 258:1235–1241, (1983)).

A potential obstacle to cloning restriction-modification genes lies in trying to introduce the endonuclease gene into a host not already protected by modification. If the methylase gene and endonuclease gene are introduced together on a single DNA segment, the methylase must protectively modify the host DNA before the endonuclease has the opportunity to cleave it. Another obstacle to cloning restriction-modification systems in *E.coli* was discovered in the process of cloning diverse methylases. Many *E. coil* strains have systems that resist the introduction of DNA containing methylated cytosine. (Raleigh and Wilson, *Proc. Natl. Acad. Sci. USA* 83:9070–9074, 1986). Therefore, it is necessary to carefully consider which E.coli strain(s) to use for cloning, and to avoid those that react adversely to modification.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided a clone containing the genes for the AccI restriction endonuclease and modification methylase derived from *Acinetobacter calcoaceticus*, as well as related methods for the production of the enzymes. More specifically, this invention relates to clones which express the restriction endonuclease AccI, which recognizes the DNA sequence 5' . . . GT(AC)(GT)AC . . . 3' and cleaves after the first T.

The preferred method for cloning this enzyme comprises forming a library containing the DNA from *Acinetobacter calcoaceticus*, isolating those clones which contain DNA coding for the AccI modification methylase and screening these to identify those that also contain the AccI restriction endonuclease gene.

DETAILED DESCRIPTION OF THE INVENTION

The present invention relates to clones of the AccI restriction and modification genes, as well as to the restriction endonuclease, AccI, produced from such clones. The AccI genes are preferably cloned by a method which takes advantage of the fact that certain clones which have been selected on the basis of containing and expressing the AccI modification methylase gene also contain the AccI restriction gene. The DNA of such clones is resistant to digestion, in vitro, by the AccI restriction endonuclease. This resistance to digestion affords a means for selectively isolating clones encoding the AccI methylase and restriction endonuclease.

Figure 1:
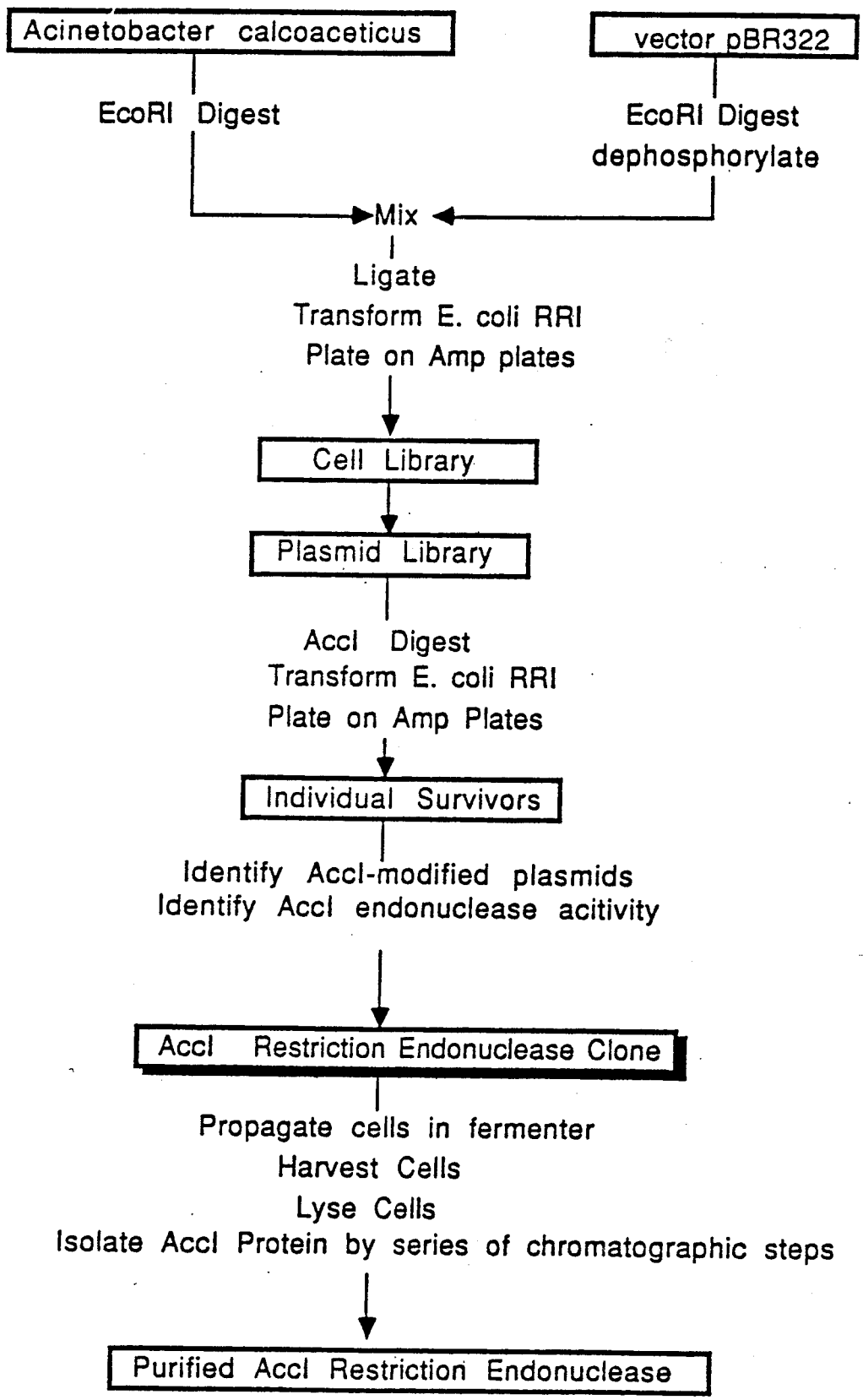
FIG. 1 illustrates the scheme for cloning and producing the AccI restriction endonuclease.

The methods described herein by which AccI restriction gene and methylase gene are preferably cloned and expressed are illustrated in FIG. 1 and include the following steps:

1. The DNA of *Acinetobacter calcoaceticus* is purified. Samples of this organism are available from The American Type Culture Collection, No. ATCC 53702.

2. The DNA is digested partially with a restriction endonuclease such as EcoRI.

3. The digested DNA is ligated to cloning vector, such as pBR322 (ATCC 37017), that contains one or more AccI sites. The ligated mixture is transformed into an appropriate host cell such as *E.coli* RRI (ATCC 31343).

4. The transformed mixture is plated on antibiotic media selective for transformed cells, such as ampicillin. After incubation, the transformed cell colonies are collected together into a single culture, the cell library.

5. The recombinant plasmids are purified in toto from the cell library to make a plasmid library.

6. The plasmid library is then digested to completion in vitro with AccI restriction endonuclease (available from New England Biolabs, Inc., Catalog #161). AccI restriction endonuclease digestion results in the differential cleavage of unmodified, non-methylase-containing clones, increasing the frequency of AccI methylase-carrying clones among the surviving intact plasmids. After digestion, the library is treated with phosphatase to further reduce the ability of digested molecules to transform.

7. The digested plasmid library is transformed back into a host such as *E. coli* strain RR1, and transformed colonies are again obtained by plating on antibiotic plates. The colonies are picked and individually analyzed for the presence of the AccI modification gene in the following manner: The plasmid DNA that they carry is purified and incubated in vitro with AccI restriction endonuclease to determine whether or not it is resistant to digestion by AccI. The total cellular DNA (chromosomal and plasmid) from the clones is also purified and incubated with AccI restriction endonuclease. The DNA of clones that carry the AccI methylase gene should be fully methylated and, both the plasmid DNA and the total DNA should be found to be substantially, or completely resistant to digestion.

8. Clones carrying the AccI restriction endonuclease are identified by preparing crude extracts of the clones identified in step 7 as carrying the AccI methylase gene, and assaying the crude extract for AccI restriction endonuclease activity. Detection of AccI restriction endonuclease activity in crude cell extracts is enhanced if the extracts are prepared from an endoA-strain of *E. coli*, such as MM294 (ATCC 33625), into which the plasmids have been transferred by transformation.

9. The quantity of AccI restriction endonuclease produced by the clones may be increased by elevating the gene dosage, through the use of high copy number vectors, and by elevating the transcription rate, through the use of highly active, exogenous promotors.

10. The AccI restriction endonuclease may be produced from clones carrying the AccI restriction and modification genes by propagation in a fermenter in a rich medium containing ampicillin. The cells are thereafter harvested by centrifugation and disrupted by sonication to produce a crude cell extract containing the AccI restriction endonuclease activity.

11. The crude cell extract containing the AccI restriction endonuclease activity is purified by standard protein purification techniques such as affinity-chromatography and ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE

Cloning of AccI Restriction Endonuclease Gene

1. DNA purification: 8 g of *Acinetobacter calcoaceticus (ATCC* 53701 ... ) cell paste was resuspended in 32 ml of 25% sucrose, 50 mM Tris pH 8.0. 16 ml of 0.25M EDTA pH 8.0, and 10 ml of 10 mg/ml lysozyme in 0.25M Tris pH 8.0, were added and the mixture was left on ice for 2 hours. 40 ml of 1% Triton X-100, 50 mM Tris pH 8.0, 62 mM EDTA and 1 ml of 10% SDS were added and the solution was mixed to achieve lysis. The suspension was extracted twice with 90 ml of freshly equilibrated (0.5M Tris, pH 8.0) phenol and 90 ml of chloroform, then centrifuged at 10K rpm for 30 min. The viscous upper layer was transferred to dialysis tubing and dialyzed against four changes of DNA buffer (10 mM Tris pH 7.5, 1 mM EDTA). The dialysed solution was transferred to a 400 ml beaker, and its volume was determined (150 ml). 1.5 ml of 10 mg/ml RNase was added to achieve 100 ug/ml RNase and the solution was incubated at 37° C. for one hour. 13 ml of 5M NaCl was mixed into the solution, 92 ml of isopropanol was layered on the top, and the solution was stirred in with a glass rod. The bacterial DNA wrapped around the glass rod as it precipitated, and was removed, air-dried, and dissolved in 6 ml of DNA Buffer.

2. Partial digestion: 800 ul of 10 mM Tris pH 7.5, 10 mM $MgCl_2$, 10 mM mercaptoethanol, 100 mM NaCl containing 80 ug of purified DNA was prepared and 100 ul aliquots were dispensed into 8 separate tubes. 10 units of EcoRI restriction endonuclease was added to the first tube to achieve 1.0 unit/ug of DNA. 5 units of EcoRI was added to the second tube (0.5 units/ug), and so on, each succeeding tube receiving half of the previous amount of EcoRI. The tubes were incubated at 37° C. for one hour, then heat-treated at 72° C. for 15 minutes and 10 ul from each analyzed by agarose gel electrophoresis. Tubes which exhibited moderate, but incomplete, digestion were chosen as the source of partial digest fragments for cloning. (These were the 0.5 u/ug, 0.25.u/ug, and 0.125 u/ug tubes. The three solutions were mixed together and used as described below).

3. Ligation: 4.0 ug (40 ul) of EcoRI partially-digested *A. calcoaceticus* DNA was mixed with 2.0 ug (20 ul) of EcoRI-cleaved and dephosphorylated pBR322 (ATCC 37017). 20 ul of 5X ligation mix (250 mM Tris pH 7.5, L$_2$50 mM MgC 50 mM DTT, 5 mM ATP) was added plus 16 ul of sterile distilled water to bring the final volume to 100 ul. 4 ul of T4 DNA ligase was added and the mixture was incubated at 16° C. for 4 hours. The ligated DNA were used to transform *E. coli* strain RRI (ATCC 31343) as follows: 50 ul of the ligated DNA was mixed with 450 ul of SSC/CaCL (50 mM NaCl, 5 mM Na$_3$Citrate, 67 mM CaL$_2$) on ice and 1200 ul of ice-cold competent *E. coli* RR1 cells (hsdR$^-$M$^-$,McrB[31]) were added. After a 3-minute heat shock at 43° C., the cells were diluted into 10 ml of Luria-broth (L-broth) and grown to saturation at 37° C.

4. Cell Library: The transformed cell culture was centrifuged, the supernatant was discarded and the cells were resuspended in 1 ml of Luria broth. 200 ul portions were plated onto Luria-agar (L-agar) plates containing 100 ug/ml ampicillin. After overnight incubation at 37° C., the plates were each flooded with 2.5 ml of 10 mM Tris pH 7.5, 10 mM $MgCl_2$ and the transformed colonies were scraped together and pooled to form the cell library.

5. Plasmid Library: 2.5 ml of the cell library was inoculated into 500 ml of L-broth containing 100 ug/ml ampicillin. The culture was shaken overnight at 37° C. and then centrifuged at 4K rpm for 5 minutes. The supernatant was discarded and the cell pellet was resuspended in 10 ml of 25% sucrose, 50 mM Tris pH 8.0, at room temperature. 5 ml of 0.25M EDTA pH 8.0, was added, followed by 3 ml of 10 mg/ml lysozyme in 0.25M Tris, pH 8.0. The solution was left on ice for 1 hour, then 12 ml of lytic mix (1% Triton X-100, 50mM Tris pH 8.0, 67 mM EDTA) was forcefully pipetted in and the cell suspension gently swirled to achieve lysis. After lysis, the mixture was transferred to a 50 ml plastic centrifuge tube and spun at 15Krpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of 5 mg/ml ethidium bromide in 10 mM Tris pH 8.0, 1 mM EDTA, 100 mM NaCl was added to the mixture. The solution was transferred to two $\frac{5}{8} \times 3$ in. polyallomer centrifuge tubes and sealed. These were then spun in the Ti70 rotor for 42 hours at 44K rpm, 17° C. To collect the plasmids, the tops of the tubes were pierced with a scalpel and the lower of the two flourescent DNA bands was collected by syringe under ultraviolet light. The lower band from both tubes was combined into a screw-top glass tube and the ethidium bromide was removed by extracting four times with an equal volume of ice-cold N-Butanol.

The extracted solution was transferred to dialysis tubing and dialyzed for 24 hours against 4 changes of DNA buffer. The dialyzed DNA solution was transferrred to a 15 ml plastic screw-cap tube. The plasmid DNA concentration was approximately 100 ug/ml.

6. Digestion of the Plasmic Library: 5 UG of plasmid DNA was digested in 200 ul of mM Tris pH7.5, 10 mM MgCL$_2$, 10 mM mercaptoethanol, 50 mM NaCl with 20 units of AccI restriction endonuclease. The tube was incubated at 37° C. for 1 hour then digestion was terminated by heating to 72° C. for 10 minutes. The solution was extracted once with equal volumes of phenol and chloroform, then the DNA was precipitated by the addition of 400 ul of isopropanol. The precipitated DNA was collected by centrifugation and resuspended in 20 ul of DNA buffer (pH 9.0) to achieve 250 ug/ml DNA. 0.4 units of bacterial alkaline phosphatase was added and the tube was incubated at 68° C. for two hours. 80 ul of DNA buffer and 80 ul of chloroform was added; the mixture was emulsified by vigorous mixing, then clarified by centrifugation. The dephosphorylated DNA was re-precipitated with isopropanol and digested again with 12 units of AccI in a 100 ul reaction volume.

7. Transformation: 12.5 ul of the AccI-digested and phosphatase-treated plasmid library was transformed into *E. coli* RR1. The cell/DNA mixture was plated onto L-agar plates containing 100 ug/ml ampicillin and incubated overnight at 37° C. Approximately 60 surviving colonies were found on the plates. 28 of these were each inoculated into 10-ml of L-broth containing ampicillin, to prepare minicultures, and streaked onto L-agar plates containing ampicillin to prepare master stocks.

8. Analysis of surviving individuals: 28 surviving colonies were grown into 10 ml cultures and the plasmids that they carried were prepared by the following miniprep purification procedure, adapted from the method of Birnboin and Doly *Nucleic Acids Res.* 7:1513 (1979).

Miniprep Procedure: Each culture was processed as follows: The 10 ml overnight culture was pelleted at 8Krpm for 5 minutes. The supernatant was poured off and the cell pellet was resuspended in 1.0 ml of 25 mM Tris pH 8.0, 10 mM EDTA, 50 mM glucose, containing 1 mg/ml lysozyme. After 10 minutes at room temperature, 2.0 ml of 0.2M NaOH, 1% SDS was added and the tube was shaken to lyse the cells, then placed on ice. Once the solution had cleared, 1.5 ml of 3M sodium acetate pH 4.8, was added and shaken. The precipitate that formed was spun down at 15Krpm, 4° C. for 10 minutes. The supernatant was poured into a centrifuge tube containing 3 ml of isopropanol and mixed. After 10 minutes at room temperature, the tube was spun at 15K rpm for 10 minutes to pellet the precipitated nucleic acids. The supernatant was discarded and the pellet was air-dried at room temperature for 30 minutes. Once dry, the pellet was resuspended in 500 ul of DNA buffer and transferred to an Eppendorf tube. The solution was extracted once with phenol and chloroform and then again precipitated with isopropanol. The tube was spun for 2 minutes in a microfuge, the supernatant was discarded and the pellet was air-dried. The pellet was then dissolved in 100 ul of DNA buffer containing 100 ug/ml RNase and incubated for 1 hour at 37° C. After incubation the plasmid minipreps were stored at −b 20° C., then analyzed by digestion with AccI and EcoRI.

Figure 2:
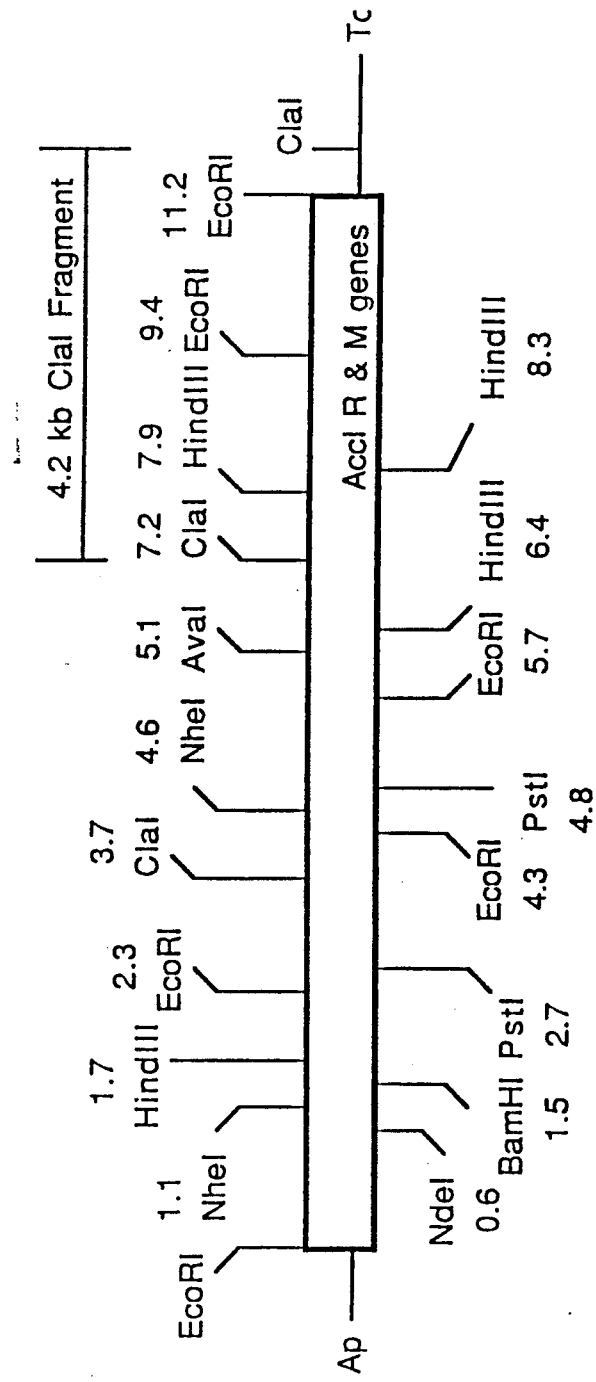
FIG. 2 is a restriction map of an 11 Kb EcoRI multifragment of *A.calcoaceticus* DNA, encoding the AccI restriction endonuclease and modification methylase, that was ligated into the EcoRI site of pBR322 (ATCC 37017) to create pSC161RM 1-8.
Figure 3:
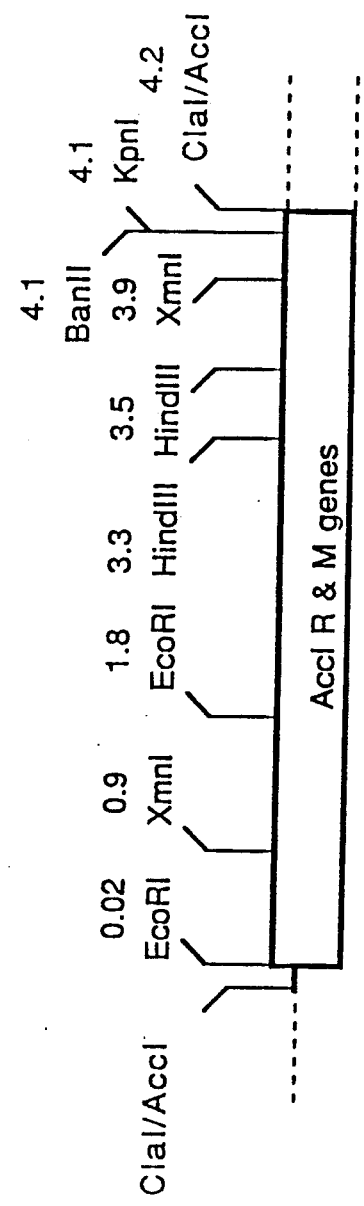
FIG. 3 is a restriction map of a 4Kb ClaI sub-fragment, encoding the AccI restriction endonuclease and modification methylase, that was excised from pSC161RM 1-8 and ligated into the AccI site of pUC19 (ATCC 37254) to create pSC161RM 121-2.

9. Methylase Gene Clones: Approximately half of the plasmids that were analysed were found to carry random EcoRI fragments of *A.calcoaceticus* DNA and to be sensitive to digestion by AccI. These plasmids were spurious survivors and were discarded. The remaining plasmids were found to be resistant to AccI and to carry up to five EcoRI fragments of approximately 3.8, 2.5, 2.4, 1.8 and 1.2 Kb in length (FIG. 2). One of the plasmids that contained all five fragments, pSC161RM 1 8, was analyzed further and was found to carry both the AccI modification methylase and restriction endonuclease genes.

10 Restriction Gene Clones: pSC161RM 1–8 was found to carry the AccI restriction endonuclease gene by assaying an extract prepared from *E.coli* strain MM294 (ATCC 33625) into which the plasmid had been transferred by transformation.

Endonuclease Assays: To assay for endonuclease activity, two solutions were prepared:(1) 10× restriction endonuclease buffer: 100 mM Tris pH 7.5, 100 mM MgCL₂, 100 mM mercaptoethanol, 500 mM NaCl; and (2) digestion reaction mix: 100 ul lambda-DNA (500 ug/ml), 100 ul 10×restriction endonuclease buffer, 800 ul distilled water to achieve 50 ug/ml DNA.

Cell extracts were prepared as follows: A 50 ml culture of the clone was grown overnight in L-broth plus 100 ug/ml ampicillin and the cells were pelleted by centrifugation at 4K rpm for 5 minutes. The supernatant was discarded and the pellet was resuspended in 3 ml of sonication buffer (10 mM Tris pH 7.5, 10 mM mercaptoethanol, 0.1 mM EDTA). Once resuspended, 0.3 ml of sonication buffer containing 10 mg/ml lysozyme was added. The suspension was swirled and left on ice for 1 hour. A 1 ml sample was transferred to an Eppendorf tube and sonicated gently for three 10-second bursts to disrupt the cells. The tube was spun for 5 minutes in a microfuge and the supernatant was used as the cell extract.

To assay the extract, the digestion reaction mix was dispensed into 5 tubes, 150 ul into the first tube and 102.5 ul into each of the remaining 4 tubes. 7.5 ul of the extract was added to the first tube and mixed. 47.5 ul was removed from the first tube and transferred to the second tube, mixed, and transferred again, and so on. The first tube thus received 1 ul of extract/ug of DNA, the second tube 0.3 ul/ug, the third tube, 0.1 ul/ug and so on. The tubes, each now containing 100 ul, were incubated at 37° C. for one hour, then a 20 ul sample of each analyzed by gel electrophoresis.

Extracts of MM294 carrying pSC161RM 1–6 were found to contain approximately 50 units of AccI restriction endonuclease per ml.

11. Isolation of the 4.2 Kb ClaI fragment from pSC161RM 1-8: 150 ul (15 ug) of purified pSC161RM 1-8 DNA was digested in 500 ul of 50 mM Tris pH8.0, 50 mM NaCl, 10M MgCl₂ with 30 units (6 ul) of ClaI restriction enzyme at 37° for 2 hours. The digestion was terminated by heating at 72° C. for 10 minutes. The solution was electrophoresed through a 1% agarose slab gel prepared, and run, in TAE buffer (40 mM Tris pH 8.2, 20 mM NaAcetate, 1 mM EDTA), with 0.01% SDS and 0.5 ug/ml ethidium bromide. The 4.2Kb band was excised under UV illumination. The gel slices were placed in a 5 ml syringe and forced through a #21 gauge needle into a 50 ml centrifuge tube containing 3 ml of TAE and 0.01% SDS, and mixed gently with a small glass rod. The tube was spun at 17K rpm for 45 minutes. The supernatant was transferred to another 50 ml centrifuge tube and 300 ul of 5M NaCl and 6 ml of 100% isopropanol were added. The tube was stored at −70° C. for one hour then centrifuged again at 17K rpm for 15 minutes. The DNA pellet was suspended in 400 ul of DNA buffer. The solution was extracted once with equal volumes of phenol and chloroform, and three times with water-equilibrated ether. The fragment was re-precipitated with 0.8 ml of isopropanol, then it was resuspended in 20 ul of DNA buffer. The purity and concentration of the fragment were determined by gel electrophoresis.

12. Ligation of the 4.2Kb ClaI fragment to pUCl9: 0.5 ug (7 ul) of the purified fragment was mixed with 1 ug (2 ul) of AccI-cleaved and dephosphorylated pUC19 (ATCC 37254) in 30 ul of ligation buffer (50 mM Tris, pH 7.5, 10 mM MgCl₂, 40 mM DTT, 1 mM ATP). 1.5 ul of T4 DNA ligase was added and the mixture was incubated at 16° C. for 4 hours. 15 ul of the ligated mixture was transformed into *E. coli* MM294 and the transformants were recovered by plating on L-Agar plates containing ampicillin. Seven transformants were screened by the miniprep procedure (Section 8). Six of these appeared to have incorporated the fragment. An extract of one of them, pSC161RM 121-2 was assayed for AccI endonuclease activity (section 10). It was found to synthesize approximately ten times more AccI endonuclease than the original clone, pSC161RM 1-8, that is, 500 units per ml of extract. The total DNA from MM294 carrying pSC161RM 121-2 was purified; it was found to be resistant to digestion by AccI, confirming that the clone produces the AccI methylase as well as the endonuclease.

Figure 4:
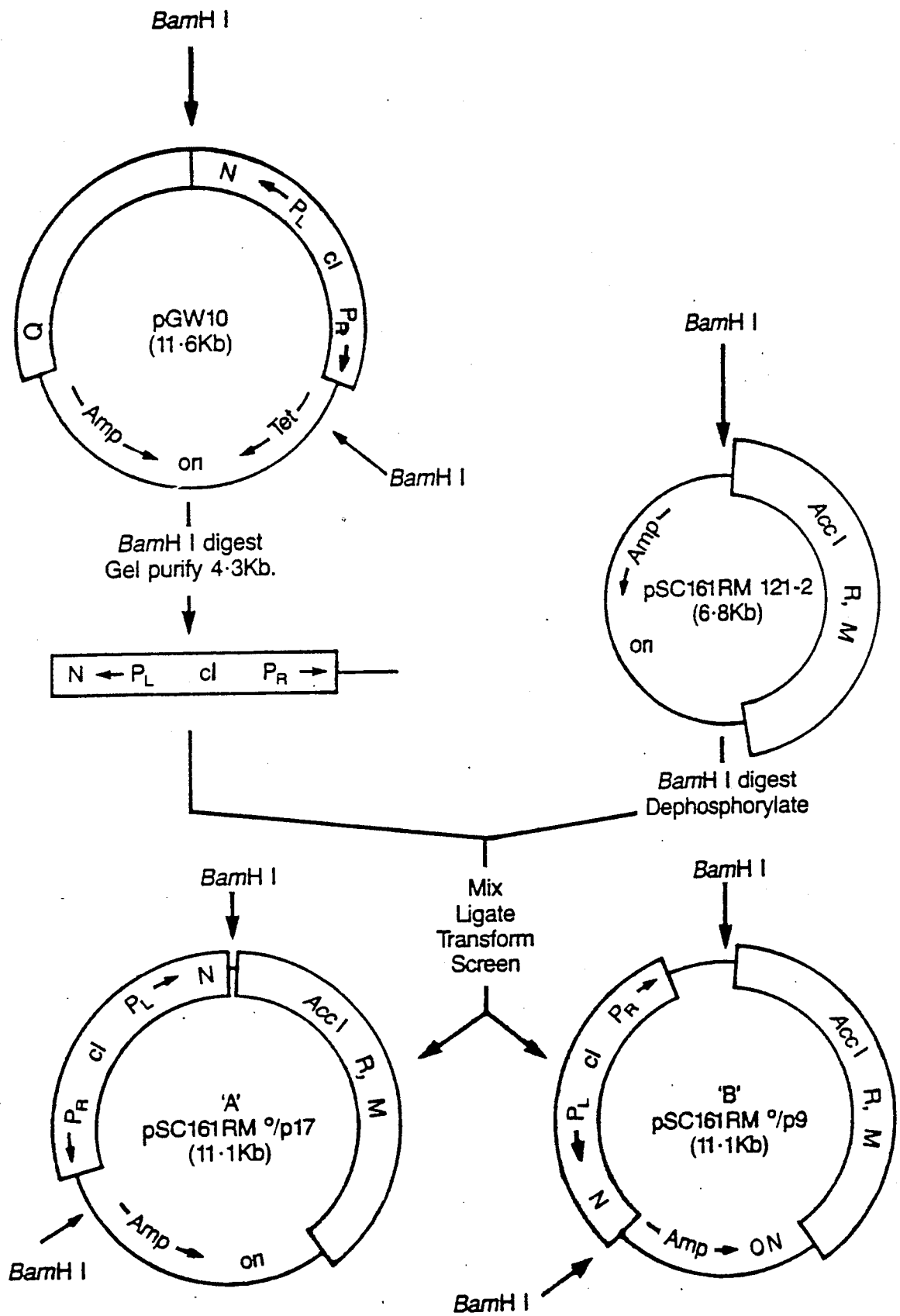
FIG. 4 illustrates the procedure used to construct the AccI endonuclease-overproducing plasmids, pSC161RM O/P9 and pSC161RM O/P17, by inserting a BamHI expression-regulation fragment from the plasmid pGW10 (ATCC 40167) into pSC161RM 121-2.
Figure 5:
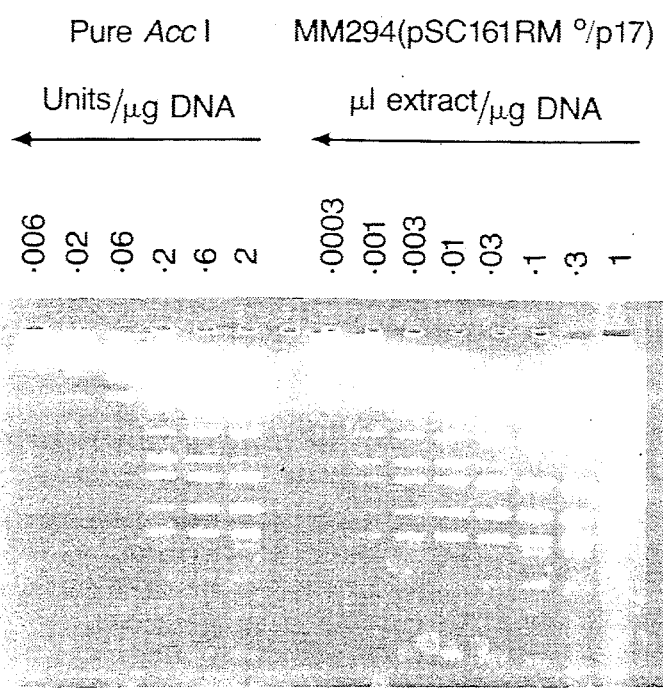
FIG. 5 is a photograph of an agarose gel illustrating AccI restriction endonuclease activity in a crude cell extract of temperature-induced *E. coli* MM294 (ATCC 33625) carrying pSC161RM O/P17.

13. Construction of AccI-overproducing plasmids: Refer to FIG. 4. 20 ug (200 ul) of the plasmid pGW10 (ATCC 40167) was digested with 80 units of BamHI in 500 ul of 6 mM Tris pH7.9, 6 mM MgCl$_2$, 150 mM NaCl, at 37° C. for 1 hour. The 4.3 kb BamHI fragment, containing the temperature-regulated lambda P$_L$ and P$_R$ promotors, was gel-purified (section 11). 0.3 ug (3 ul) of the purified fragment was mixed with 0.6 ug (6 ul) of BamHI-cleaved, dephosphorylated pSC161RM 121-2 in 25 ul of ligation buffer (section 12). 1 ul of T4 DNA ligase was added and the mixture was incubated at 16° C. for 4 hours. 15 ul of the ligated mixture was transformed into E. coli MM294 and transformants were recovered by plating onto L-Agar plates containing ampicillin, and incubated at 30° C. for 24 hours. 24 transformants were selected for analysis. They were initially screened to streaking onto duplicate L-agar plates containing ampicillin and incubating one plate at 30° C. and the other at 42° C. Four of the 24 transformants grew at 42° C. and were discarded. Fourteen of the twenty remaining, temperature-sensitive, transformants were analyzed by the miniprep procedure (Section 8). Twelve of these were found to have incorporated the BamHI fragment, eleven in one orientation ('B'), and one in the other orientation ('A'). The two remaining two clones that had not incorporated the fragment were discarded.

The 'A'-orientation clone, pSC161RM O/P17, and one of the 'B'-orientation clones, pSC161RM O/P9 were assayed to determined the quantity of AccI endonuclease that they synthesized. 100 ml cultures of each were grown at 30° C. in L-broth containing ampicillin. At a cell density of approximately $3 \times 10^8$ cells/ml (optical density at 590 nm=0.8 to 1.0), 50 ml from each culture was shifted to an incubation temperature of 42° C. After three hours further incubation the 30° C. and 42° C. cultures were centrifuged and cell extracts were prepared from them and assayed (Section 10). The 'A' orientation clone was found to synthesize approximately 30,000 units of AccI endonuclease/ml of cell extract at 42° C., and less than 100 units/ml at 30° C. In this plasmid, the lambda P$_L$ promotor was found to be oriented in the clockwise direction (FIG. 4). The 'B' orientation clone, in which the promotor has the opposite orientation, was found to synthesize approximately 3000 units of AccI endonuclease/ml of extract at both 42° C. and 30° C. Acinoetobacter calcoaceticus also synthesizes approximately 3000 units of AccI endonuclease/ml of extract when it is grown under optimum conditions.

E. coli MM294 containg PSC161RM O/P17 is the preferred source from which the AccI restriction endonuclease can be purified. A sample of psC161M O/P17 has been deposited at the american Type Culture Collection under ATCC Accession No. 40897. Cultures of this strain should be grown at 30° C. to late-log phase ($5 \times 10^8$ cells/ml) then shifted to 42° C. for a further 3 hours, to induce transcription from the lambda promotor. The cells should then be collected by centrifugation and an extract prepared from them either immediately, or after storage at −70° C.

What is claimed is:

1. Isolated DNA coding for the AccI restriction endonuclease, wherein the isolated DNA is obtainable from the vector pSC161RMO/P17.

2. A recombinant DNA vector comprising a vector into which a DNA segment coding for the AccI endonculease produced from Acinetobacter calcoaceticus ATCC No. 53701 has been inserted.

3. Isolated DNA coding for the AccI restriction endonclease and methylase, wherein the isolated DNA is obtainable from the vector pSC161RMO/P17.

4. A cloning vector which comprises the isolated DNA of claim 3.

5. The cloning vector of claim 4, wherein the cloning vector comprises psC161RMO/P17.

6. A host cell transformed by the vector of claim 2, 4 or 5.

7. A method of cloning DNA coding for an AccI restriction endonculease comprising:
   (a) purifying DNA from Acinetobacter calcoaceticus ATCC No. 53701;
   (b) partially digesting the purified DNA with EcoRI to form DNA fragments;
   (c) ligating the DNA fragments into a cloning vector;
   (d) transforming a host cell with the cloning vector of step (c) to form a cell library;
   (e) purifying recombinant vectors from the cell library to form a plasmid library;
   (f) contacting the plasmid library of step (e) with AccI to form a digestion pool, transforming the digestion pool into a host cell, and screening for the presence of one or more cloning vectors containing DNA coding for an AccI methylase;
   (g) transferring the cloning vector of step (f) which contains DNA coding for AccI methylase into E. coli MM294 and screening for the presence of DNA coding for an AccI restriction endonuclease; and
   (h) isolating the cloning vector of step (g) which contains DNA coding for AccI restriction endonuclease.

8. A method of producing AccI restriction endonuclease comprising culturing a host cell transformed with the vector of claim 2, 4 and 5 under conditions suitable for the expression of said endonculease.

9. A method for producing AccI restriction endonuclease comprising:
   (a) purifying DNA from Acinetobacter calcoaceticus ATCC No. 53701;
   (b) partially digesting the purified DNA with EcoRI to form DNA fragments;
   (c) ligating the DNA fragments into a cloning vector;
   (d) transforming a host cell with the cloning vector of step (c) to form a cell library;
   (e) purifying recombinant vectors from the cell library to form a plasmid library;
   (f) contacting the plasmid library of step (e) with AccI to form a digestion pool, transforming the digestion pool into a host cell, and screening for the presence of one or more cloning vectors containing DNA coding for an AccI methylase;
   (g) transferring the cloning vector of step (f) which contains DNA coding for AccI methylase into E. coli MM294 and screening for the presence of DNA coding for an AccI restriction endonuclease;
   (h) isolating the cloning vector of step (g) which contains DNA coding for AccI restriction endonculease; and
   (i) culturing a host cell transformed with the cloning vector of step (h) under conditions suitable for expression of AccI restriction endonculease.

* * * * *

UNITED STATES PATENT AND TRADEMARK OFFICE
CERTIFICATE OF CORRECTION

PATENT NO.   : 5,004,691
DATED        : April 2, 1991
INVENTOR(S)  : Chen et al.

It is certified that error appears in the above-identified patent and that said Letters Patent is hereby corrected as shown below:

Col. 4, line 7, "ATCC 53702" should be --ATCC 53701--.

Col. 5, line 18, "53701..." should be --53701--.

Signed and Sealed this

Twentieth Day of April, 1993

Attest:

MICHAEL K. KIRK

*Attesting Officer*          *Acting Commissioner of Patents and Trademarks*